United States Patent

Sakuma et al.

Patent Number: 5,364,890
Date of Patent: Nov. 15, 1994

[54] DENTAL ADHESIVE COMPOSITION

[75] Inventors: Tetsuro Sakuma, Tokorozawa; Junichi Okada, Noda, both of Japan

[73] Assignee: GC Corporation, Tokyo, Japan

[21] Appl. No.: 67,174

[22] Filed: May 26, 1993

Related U.S. Application Data

[63] Continuation of Ser. No. 911,512, Jul. 10, 1992, abandoned.

[30] Foreign Application Priority Data

Oct. 11, 1991 [JP] Japan .................... 3-290422

[51] Int. Cl.$^5$ .............................. A61K 6/08
[52] U.S. Cl. ........................ 522/92; 106/35; 523/118
[58] Field of Search .......... 106/35; 523/109–116; 433/228.1; 564/252; 526/217, 328, 329.7; 522/92

[56] References Cited

U.S. PATENT DOCUMENTS

| | | | |
|---|---|---|---|
| 4,525,493 | 6/1985 | Omura et al. | 523/116 |
| 4,778,471 | 10/1988 | Bajpai. | |
| 5,105,010 | 4/1992 | Sundararaman et al. | 564/252 |
| 5,136,006 | 8/1992 | Sundararaman et al. | 526/312 |

FOREIGN PATENT DOCUMENTS 55-164611  12/1980  Japan ..................... A61K 6/08

*Primary Examiner*—Paul Lieberman
*Assistant Examiner*—Margaret Einsmann
*Attorney, Agent, or Firm*—Oblon, Spivak, McClelland, Maier & Neustadt

[57] ABSTRACT

A compound having a carbodiimide in its molecule is incorporated in a dental adhesive composition. With this composition, dental composite material can be firmly bonded to the enamel and dentin of a tooth, thereby avoiding formation of a gap which may otherwise cause secondary caries.

20 Claims, No Drawings

DENTAL ADHESIVE COMPOSITION

This application is a continuation of application Ser. No. 07/911,512, filed on Jul. 10, 1992, now abandoned.

BACKGROUND OF THE INVENTION

This invention relates to a dental adhesive composition for bonding acrylic resin to teeth and, more specifically, to a dental adhesive composition for restorative teeth and for bonding dental composite material (composite resin) to enamel and dentin. A bonding force with respect to dentin is particularly needed for restorative teeth.

With a conventional adhesive for bonding restorative composite resin to an enamel, a bonding strength higher than 100 kg/cm$^2$ that meets clinical requirements well enough is obtained between an enamel and the restorative composite resin. This is true even when an enamel is treated by acid etching using phosphoric or citric acid, then washed with water and dried, and finally coated with a primer which is composed of a methacrylic ester monomer and a curing agent and shows no adhesion to the dentin. However, as only poor adhesion to a dentin is obtained by using the primer having no adhesion to the dentin, various dentin treatment solutions or primers considered to be adhesive have been proposed. For instance, Japanese Patent Publication No. 55-30768 describes a phosphoric ester compound as being adhesive to the dentin, but it fails to give the aforesaid high bonding strength, as measured by the present inventors.

Japanese Patent Laid-Open No. 54-12338 discloses a functional monomer 4-methacryloxyethyl trimellitic anhydride (hereinafter 4META for short), and the "Journal of the Japan Society for Dental Apparatus and Materials", 23(61), pp. 29–32 (1982) teaches that when a dentin is treated with an aqueous solution of 10% citric acid and 3% ferric chloride and then restored with a restorative filler (4META-containing methyl methacrylate/tri-n-butyl borane/polymethyl methacrylate), a bonding strength of 12–18 Mpa is obtained. When measured by the present inventors, however, such a high bonding strength could not be obtained. Furthermore, when using a chemical polymerization type restorative composite resin made up of a redox initiating system of a tertiary amine-benzoyl peroxide, a problem will arise in connection with the reaction between the tertiary amine and 4META.

In view of the present state of the art where no clinically efficacious adhesive is obtained yet, as mentioned above, we have made an effort to achieve an adhesive which is not only improved in terms of its adhesion to a dentin but serves to reinforce a dentin as well, and so have accomplished the present invention.

SUMMARY OF THE INVENTION

As a result of strenuous studies made to provide a solution to the state-of-the-art problem mentioned above, we have now found that a dental adhesive composition containing a compound having a carbodiimide in its molecule has much higher bonding strength to a dentin than ever before. This would appear to be so because the protein component of a dentin is chemically combined with a methacrylic ester monomer having a hydroxyl or amino group due to their dehydration reaction which takes place under the catalytic action of the carbodiimide. In addition, the carbodiimide serves to crosslink dentinal protein, so that composite resin can be firmly bonded to a dentin by the dental adhesive composition containing a compound having a carbodiimide in its molecule.

DETAILED EXPLANATION OF THE INVENTION

In the ensuing description, this invention will be explained at great length.

The dental adhesive composition according to this invention is characterized by containing a compound having a carbodiimide in its molecule. Mentioned for this compound, for instance, cyclohexylcarbodiimide, 1-ethyl-3-(3-dimethylaminopropyl)carbodiimide and 1-cyclohexyl-3-(2-morpholinoethyl)carbodiimide.

These compounds should be used in an amount lying in the range of preferably 0.1 to 20.0% and more preferably 0.5 to 10.0% with respect to the total weight of the composition.

Any morphological limitation is not imposed on this dental adhesive composition, provided that it contains a compound having a carbodiimide in its molecule. For instance, it may be available in the form of a primer composition (which does not cure by itself) diluted with a solvent, a photo-polymerizable type composition, a chemically polymerizable type composition which is divided into two or more parts and a composite resin composition in which the monomer contains that compound. Preferable for this invention is a dental adhesive composition made up of:

a) a compound having a carbodiimide in its molecule,
b) a methacrylate or acrylate having at least one unsaturated double bond, and
c) a polymerization initiator.

For the methacrylate or acrylate b) which has at least one unsaturated double bond, use may be specifically made of methyl methacrylate, ethyl methacrylate, isopropyl methacrylate, hydroxyethyl methacrylate, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, 2,2-bis(methacryloxyphenyl)propane, 2,2-bis[4-(2-hydroxy-3-methacryloxypropoxy)phenyl]propane, 2,2-bis(4-methacryloxydiethoxyphenyl)propane, 2,2-bis(4-methacryloxypropoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol methacrylate, 1,4-butanediol dimethacrylate, 1,6-hexanediol methacrylate, trimethylolpropane trimethacrylate, trimethylolethane trimethacrylate, pentaerythritol trimethacrylate, trimethylolmethane trimethacrylate and pentaerythritol tetramethacrylate and their acrylates as well as methacrylates and acrylates containing an urethane bond in their molecules. Note that particular preference is given to di-2-methacryloxyethyl-2,2,4-trimethylhexamethylene dicarbamate or its acrylate as well as compounds having the following structural formula:

Structural Formula 1

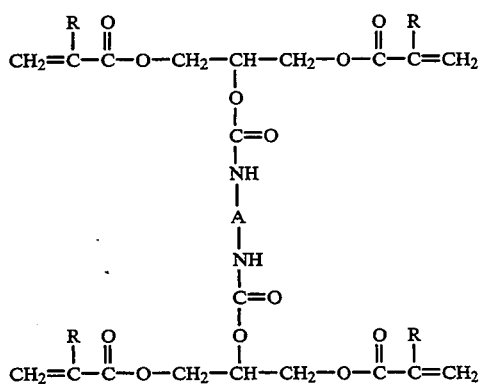

wherein:
Rs may be identical with or different from each other and each stand H or CH₃, and

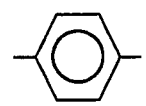
Structural formula 2

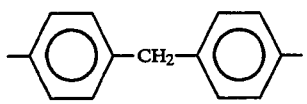
Structural formula 3 are preferable.

These methacrylates and acrylates themselves are known as dental materials and may be used alone or in admixture if need be.

In recent years, photopolymerization initiators have often been used as the polymerization initiator c), and for them sensitizer-reducer combinations are now generally used. The sensitizers used, for instance, may include camphor quinone, benzyl, diacetyl, benzyl dimethyl ketal, benzyl diethyl ketal, benzyl di-(2-methoxyethyl)ketal, 4,4'-dimethylbenzyl-dimethyl ketal, anthraquinone, 1-chloroanthraquinone, 2-chloroanthraquinone, 1,2-benzanthraquinone, 1-hydroxyanthraquionone, 1-methylanthraquinone, 2-methylanthraquinone, 1-bromoanthraquinone, thioxanthone, 2-isopropyl-thioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethyl-thioxanthone, thioxanthone-10, 10-dioxide, thioxanthone-10-oxide, benzoin methyl ether, benzoin ethyl ether, benzoin isopropyl ether, benzoin isobutyl ether, benzophenone, bis-(4-dimethylaminophenyl) ketone, 4,4'-bisdiethylaminobenzo-phenone and azid group-containing-compounds, which may be used alone or in combination of two or more.

In general, tertiary amines may be used as the the reducing agent. The tertiary amines used, for instance, may preferably include dimethylaminoethyl methacrylate, triethanolamine, 4-dimethylaminomethyl benzoate, 4-dimethylaminoethyl benzoate and 4-dimethylaminoisoamyl benzoate. Other reducing agents, for instance, benzoyl peroxide, sulfinic acid derivatives and organometal compounds, may be used as well.

The thus obtained photopolymerization type adhesive compositions are polymerized by exposure to active rays such as ultraviolet or visible rays. The light sources used to this end, for instance, may include various forms of ultrahigh, high, intermediate and low pressure mercury lamps, chemical lamps, carbon arc lamps, metal halide lamps, fluorescent lamps, tungsten lamps, xenon lamps and argon ion lasers.

As the chemical polymerization initiator, use may be made of benzoyl peroxide-tertiary amine, benzoyl peroxide-N-phenylglycine, benzoyl peroxide-sodium p-toluenesulfinate, benzoyl peroxide-sodium p-benzenesulfinate, benzoyl peroxidesodium p-toluenesulfinate with or without an aromatic tertiary amine, potassium persulfate-aromatic tertiary amine and sodium persulfate-aromatic tertiary amine combinations.

The adhesive compositions according to this invention may be used not only in primer forms but also in solvent-containing forms. In the latter case, all solvents may be used, provided that they are soluble in them. Mentioned to this end are, by way of example alone, water, methanol, ethanol, propanol, butanol, acetone, methyl ethyl ketone, methyl isobutyl ketone, toluene, xylene, ethyl acetate, butyl acetate, cellosolve, tetrahydrofuran, dioxane, dichloro-methane, chloroform, carbon tetrachloride, trichloroethylene, dimethylformamide and dimethylsulfoxide.

The adhesive compositions of this invention may include fillers as well. The usable fillers may be based on inorganic, organic materials or combination thereof. As the inorganic fillers, use may be made of, by way of example alone, powdery quartz, powdery alumina, powdery glass, kaolin, talc, zinc white, calcium carbonate, aluminosilicate glass, barium aluminosilicate glass, strontium glass, titanium oxide, boronsilicate glass and powdery colloidal silica. The organic composite fillers obtained by compacting the inorganic fillers with polymers and pulverizing the compacts may potentially be used as well.

For the organic fillers used, mention is made of, by way of example alone, polyacrylic acid, polymethacrylic acid, methyl polyacrylate, methyl polymethacrylate, methyl methacrylate-ethyl methacrylate copolymers, acrylic acid-maleic acid copolymers and crosslinked methyl polymethacrylate, and these powdery polymers may optionally be used in admixture with the aforesaid inorganic powders. Prior to being mixed with binder resins, the aforesaid inorganic fillers are generally treated on their surfaces with a silane coupling agent capable of reacting with these two. In most cases, γ-methacryloxypropyltrimethoxysilane is used as the silane coupling agent.

In the ensuing description, this invention will be explained at great length with reference to some examples in which the bonding strength of samples and the state of fitness to teeth were assessed.

HOW TO MEASURE BONDING STRENGTH

1. The surface of a fresh bovin anteriortooth was polished by a #1000 water-resistant abrasive paper while water was poured thereon until the dentinal surface was exposed to view.

2. The dentinal surface was coated with each dental adhesive composition through a cellophane tape having 3.0-mm diameter pores applied onto it, which was in turn thinly spread with the use of air.

3. Of the dental adhesive compositions, one containing a photopolymerization initiator was exposed to the light from a GC's dental irradiator (GC Light) for 20 seconds.

4. A GC photopolymerization type composite resin ("Graft LC") was built up on an adhesion surface with a 2.0 mm thick silicone rubber mold having a pore of 5.0 mm in internal diameter, and exposed to light from a GC light for 40 seconds for curing.

5. After immersed in water of 37° C. for one day, the test piece was pulled at a crosshead speed of 1.0 mm/min on an autograph made by Shimazu Company for tensile adhesion testing.

HOW TO OBSERVE FITNESS OF RESIN COMPOSITION TO TEETH

1. A saucer type cavity was formed in the axial face of a human extracted true molar.

2. According to the strength measuring procedures described above, a dental adhesive composition was coated on the tooth, and a photopolymerization type composite resin was filled in the cavity for curing. Note that the enamel was etched with phosphoric acid in a conventional manner.

3. After cured, the test piece was held in water of 37° C. for 24 hours. After that, the central region of the cavity was horizontally cut perpendicularly with respect to the axis, and the section was smoothened with a No. 1000 emery paper while water was poured thereon.

4. After the section was slightly corroded with a phosphoric acid solution, a precision replica of that section was formed. In what state the resin was bonded to the dentinal surface was examined by observing the replica surface under an SEM.

5. Fitness assay was made according to Sasazaki's method for measuring resin/dentin gaps (cf. "The Japanese Journal of Conservative Dentistry", Vol. 28, No. 2, pp. 452–478 (1985)). The assay was made according to five ranks a, b, c, d and e, vs. a: no gap found, indicating that excellent fitness is achieved.
  b: a slight gap.
  c: a gap of 5 $\mu$m or less.
  d: a gap of 5–10 $\mu$m.
  e: a gap of 10 $\mu$m or more.

EXAMPLE 1

| Liquid A | |
|---|---|
| Dicyclohaxylcarbodiimide | 5.0 wt % |
| N-phenylglycine | 1.0 wt % |
| Ethanol | 94.0 wt % |
| Liquid B | |
| 2-Hydroxymethacrylate | 30.0 wt % |
| 2,2-bis[4-(2-hydroxy-3-methacryl-oxypropoxy)phenyl]propane | 30.0 wt % |
| Benzoyl peroxide | 1.0 wt % |
| Ethanol | 39.0 wt % |

The same amounts of the liquids A and B above—which are chemically polymerizable adhesive compositions—were mixed together, and the mixture was tested according to the procedures as mentioned above. The results are set out in Table 1.

EXAMPLES 2–5

The mixtures of Liquids A and B referred to in Table 1 were tested following the procedures of Example 1. The results are set out in Table 1.

EXAMPLE 6

| | |
|---|---|
| 1-Ethyl-3(3-dimethylaminopropyl)carbodiimide | 5.0 wt % |
| 2,2-bis[4-(2-hydroxy-3-methacryloxypropoxy)phenyl]propane | 25.0 wt % |
| Hydroxyethyl methacrylate | 25.0 wt % |
| Camphor quinone | 5.0 wt % |
| Dimethylaminoethyl methacrylate | 1.0 wt % |
| Ethanol | 43.6 wt % |

A photopolymerizable type adhesive composition composed of the component above was tested following the procedures of Example 1. The results are set out in Table 2.

EXAMPLES 7–9

Photopolymerizable type adhesive compositions consisting of the components referred to in Table 2 were tested following the procedures of Example 1. The results are set out in Table 2.

EXAMPLE 10

A primer type adhesive composition consisting of

| | |
|---|---|
| 1-Ethyl-3(3-dimethylaminopropyl)carbodiimide | 5.0 wt % |
| Ethanol | 95.0 wt % | was tested following the procedures of Example 1. The results are set out in Table 3.

EXAMPLES 11 & 12

Two primer type adhesive compositions referred to in Table 3 were tested following the procedures of Example 1. The results are set out in Table 3.

Comparative Examples 1–3

Various types of carbodiimide-free compositions referred to in Table 4 were tested following the procedures of Example 1. The results are set out in Table 4.

Comparative Examples 4 & 5

Compositions with the carbodiimide contents departing from the range defined by the invention, as referred to in Table 4, were tested following the procedures of Example 1. The results are set out in Table 4.

TABLE 1

| | Liquid A | | | Liquid B | | | Bonding Strength To Dentine (kg/cm$^2$) | Fitness |
|---|---|---|---|---|---|---|---|---|
| Example 1 | Cyclohexylcarbodiimide<br>N-phenylglycine<br>Ethanol | 5.0<br>1.0<br>94.0 | weight % | 2-hydroxy methacrylate<br>2,2-bis[4-(2-hydroxy-3-methacryloxypropoxy)phenyl]propane<br>Benzoyl peroxide<br>Ethanol | 30.0<br>30.0<br><br>1.0<br>39.0 | weight % | 131 | a |
| Example 2 | 1-ethyl-3-(3-dimethylaminopropyl)carbodiimide | 5.0 | weight % | Methylmethacrylate<br>2,2-bis[4-(2-hydroxy-3- | 30.0<br>30.0 | weight % | 150 | a |

TABLE 1-continued

|  | Liquid A |  | Liquid B |  | Bonding Strength To Dentine (kg/cm²) | Fitness |
|---|---|---|---|---|---|---|
|  | N-phenylglycine | 1.0 | methacryloxypropoxy)phenyl] |  |  |  |
|  | Acetone | 94.0 | propane |  |  |  |
|  |  |  | Benzoyl peroxide | 1.0 |  |  |
|  |  |  | Acetone | 39.0 |  |  |
| Example 3 | Cyclohexylcarbodiimide | 5.0 weight % | 2-hydroxyethyl methacrylate | 50.0 weight % | 144 | a |
|  | 2-hydroxyethyl methacrylate | 20.0 | Benxoyl peroxide | 1.0 |  |  |
|  | p-toluenesulfinate | 1.0 | Ethanol | 49.0 |  |  |
|  | Ethanol | 74.0 |  |  |  |  |
| Example 4 | 1-cyclohexyl-3-(2-morpholineoethyl) carbodiimide | 5.0 weight % | Methylmethacrylate | 39.0 weight % | 138 | a |
|  |  |  | 2-hydroxyethyl methacrylate | 30.0 |  |  |
|  | Methylmethacrylate | 50.0 | 2,2-bis[4-(2-hydroxy-3- | 30.0 |  |  |
|  | 2-hydroxy methacrylate | 44.0 | methacryloxypropoxy)phenyl] |  |  |  |
|  | N,N-dihydroxyethyl p-toluidine | 1.0 | propane |  |  |  |
|  |  |  | Benzoyl peroxide | 1.0 |  |  |
| Example 5 | Cyclohexylcarbodiimide | 1.0 weight % | Triethyleneglycol di- | 49.0 weight % | 129 | a |
|  | 2-hydroxyethyl methacrylate | 50.0 | methacyrlate | 50.0 |  |  |
|  | Isobutyl methacrylate | 47.0 | 2,2-bis[4-(2-hydroxy-3- |  |  |  |
|  | N,N-dihydroxypropyl p-toluidine | 1.0 | methacryloxypropoxy)phenyl] |  |  |  |
|  | p-toluenesulfinate | 1.0 | propane |  |  |  |
|  |  |  | Benzoil peroxide | 1.0 |  |  |

TABLE 2

|  | Photopolymerization Type |  | Bonding Strength To Dentin (kg/cm²) | Fitness |
|---|---|---|---|---|
| Example 6 | 1-ethyl-3-(3-dimethylaminopropyl)carboiimide | 5.0 weight % | 173 | a |
|  | 2,2-bis[4-(2-hydroxy-3-methacryloxypropoxy)phenyl]propane | 25.0 |  |  |
|  | 2-hydroxyethyl methacrylate | 25.0 |  |  |
|  | Camphor quinone | 0.5 |  |  |
|  | Diemthylaminoethylmethacrylate | 1.0 |  |  |
|  | Ethanol | 43.5 |  |  |
| Example 7 | Cyclohexylcarbodiimide | 5.0 weight % | 147 | a |
|  | Di-2-methacryloxylethyl-2,2,4-trimethylhexamethylene dicarbamate | 25.0 |  |  |
|  | 2-hydroxyethyl methacrylate | 25.0 |  |  |
|  | Camphor quinone | 0.5 |  |  |
|  | Dimethylaminoethylmethacrylate | 1.0 |  |  |
|  | Acetone | 43.5 |  |  |
| Example 8 | 1-cyclohexyl-3-(2-morpholinoethyl)carbodiimide | 1.0 weight % | 153 | a |
|  | 2,2-bis[4-(2-hydroxy-3-methacryloxypropoxy)phenyl]propane | 50.0 |  |  |
|  | 2-hydroxyethyl methacrylate | 47.4 |  |  |
|  | Benzylmethylketal | 0.5 |  |  |
|  | 1,2-benzanthraquinone | 0.1 |  |  |
|  | 4-diemthylaminoethyl benzoate | 1.0 |  |  |
| Example 9 | 1-ethyl-3-(3-dimethylaminopropyl))carbodiimide | 5.0 weight % | 161 | a |
|  | Triethyleneglycol-dimethacrylate | 33.5 |  |  |
|  | Di-2-methacryloxyethyl-2,2,4-trimethylhexamethylene dicarbamate | 30.0 |  |  |
|  | Fine powdery quartz (average size 3 μm) | 30.0 |  |  |
|  | Camphor quinone | 0.5 |  |  |
|  | 4-dimethylaminoisoamyl benzoate | 1.0 |  |  |

TABLE 3

|  | Primer Types |  | Bonding Strength To Dentin (kg/cm²) | Fitness |
|---|---|---|---|---|
| Example 10 | 1-ethyl-3-(3-dimethylaminopropyl)carbodiimide | 5.0 weight % | 123 | a |
|  | Ethanol | 95.0 |  |  |
| Example 11 | 1-cyclohexyl-3-(2-morpholinoethyl)carbodiimide | 3.0 weight % | 160 | a |
|  | 2-hydroxylethylmethacrylate | 50.0 |  |  |
|  | Ethanol | 47.0 |  |  |
| Example 12 | Cyclohexylcarbodiimide | 3.0 weight % | 154 | a |
|  | Dimethylaminoethylmethacrylate | 3.0 |  |  |
|  | Acetone | 94.0 |  |  |

TABLE 4

| | Liquid A | | Liquid B | | Bonding Strength To Dentin (kg/cm²) | Fitness |
|---|---|---|---|---|---|---|
| Comparative Example 1 (Chemical polymerization Type) | p-toluenesulfinate<br>N,N-dihydroxyethyl-p-toluidine<br>Ethanol | 1.0 weight %<br>1.0<br>98.0 | 2-hydroxymethacrylate<br>2,2-bis[4-(2-hydroxy-3-methacryloxypropoxy)phenyl]propane<br>Benzoyl peroxide<br>Ethanol | 30.0 weight %<br>30.0<br><br>1.0<br>39.0 | 12 | e |
| Comparative Example 2 (Photo-polymerization Type) | 2,2-bis[4-(2-hydroxy-3-methacryloxypropoxy)phenyl]propane<br>2-hydroxyethyl methacrylate<br>Camphor quinone<br>Dimethylaminoethylmethacrylate<br>Ethanol | | | 25.0 weight %<br>25.0<br>0.5<br>1.0<br>48.5 | 2 | d |
| Comparative Example 3 (Primer) | 2-hydroxyethyl methacrylate<br>Ethanol | | | 50.0 weight %<br>50.0 | 3 | e |
| Comparative Example 4 (Photo-polymerization Type) | 1-ethyl-3-(3-dimethylaminopropyl)carbodiimide<br>Di-2-methacryloxylethyl-2,2,4-trimethylhexamethylene dicarbamate<br>2-hydroxyethylmethacrylate<br>Camphor quinone<br>Dimethylaminoethylmethacrylate<br>Ethanol | | | 0.05 weight %<br>25.0<br>25.0<br>0.5<br>1.0<br>48.45 | 5 | e |
| Comparative Example 5 | (Photopolymerization Type)<br>1-cyclohexyl-3-(2-morpholinoethyl)carbodiimide<br>2,2-bis[4-(2-hydroxy-3-methacryloxypropoxy)phenyl]propane<br>2-hydroxyethylmethacrylate<br>1,2-benzanthraquinone<br>4-dimethylaminoethyl benzoate | | | 25.0 weight %<br>40.0<br>33.9<br>0.1<br>1.0 | 1 | d |

As can be seen from Tables 1–4, it is verified that the dental adhesive compositions containing the compounds having carbodiimides in their molecules show a strong bonding strength to the dentin in particular.

From observation of fitness done with human extracted teeth, it is noted that the resins are well bonded to the dent in with no gap between them whatsoever, which is a leading cause of secondary caries.

What is claimed is:

1. A dental adhesive composition comprising
   (a) 1-ethyl-3-(3-dimethylaminopropyl)carbodiimide
   (b) at least one methacrylate or acrylate selected from the group consisting of methyl methacrylate, ethyl methacrylate, isopropyl methacrylate, 2-hydroxyethyl methacrylate, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, 2,2-bis(methacryloxyphenyl)propane, 2,2-bis[4-(2-hydroxy-3-methacryloxypropoxy)phenyl]propane, 2,2-bis(4-methacryloxydiethoxyphenyl)propane, 2,2-bis(4-methacryloxypropoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol methacrylate, 1,4-butanediol dimethacrylate, 1,6-hexanediol methacrylate, trimethylolpropane trimethacrylate, trimethylolethane trimethacrylate, pentaerythritol trimethacrylate, trimethylolmethane trimethacrylate, pentaerythritol tetramethacrylate, methacrylates and acrylates containing a urethane bond in their molecules, di-2-methacryloxyethyl-2,2,4-trimethylhexamethylene dicarbamate or its acrylate and compounds having the following structural formula:

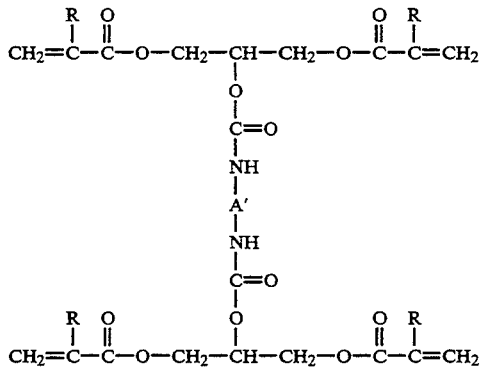

wherein:
R, which may be identical or different from each other is H or CH₃, and
A is —(CH₂)₆—,

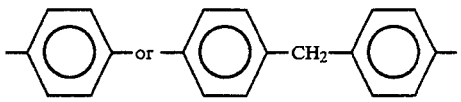

and
   (c) a photopolymerization or a chemical polymerization initiator which chemical polymerization initiator is selected from the group consisting of the following combinations:
   1) N-phenylglycine and benzoyl peroxide;
   2) p-toluenesulfinate and benzoyl peroxide; and
   3) p-toluenesulfinate, an aromatic tertiary amine and benzoyl peroxide.

2. A dental adhesive composition as claimed in claim 1, wherein said 1-ethyl-3-(3-dimethylaminopropyl)carbodiimide is present in an amount of from 0.1 to 20.0% with respect to the total weight of the composition.

3. A dental adhesive composition as claimed in claim 1, wherein said methacrylate or acrylate is present in an amount of from 50 to 97.4% with respect to the total weight of the composition.

4. A dental adhesive composition as claimed in claim 1, which further comprises an organic solvent.

5. A dental adhesive composition as claimed in claim 1, which further comprises a filler.

6. A dental adhesive composition as claimed in claim 1, wherein said 1-ethyl-3-(3-dimethylaminopropyl)carbodiimide is present in an amount of from 0.5 to 10.0% with respect to the total weight of the composition.

7. A dental adhesive composition as claimed in claim 1, wherein said methacrylate or acrylate is 2-hydroxyethylmethacrylate or triethylene glycol dimethacrylate.

8. A dental adhesive composition as claimed in claim 1, wherein said photopolymerization initiator consists of a sensitizer-reducer combination.

9. A dental adhesive composition as claimed in claim 1, wherein said at least one methacrylate or acrylate is selected from the group consisting of methyl methacrylate, 2,2-bis[4-(2-hydroxy-3-methacryloxypropoxy)phenyl]propane, 2-hydroxyethyl methacrylate, triethylene glycol dimethacrylate and di-2-methacryloxyethyl-2,2,4-trimethylhexamethylene dicarbamate.

10. A dental adhesive composition as claimed in claim 1, comprising a chemical polymerization initiator.

11. A dental adhesive composition as claimed in claim 10, wherein said chemical polymerization initiator is a combination of N-phenylglycine and benzoyl peroxide.

12. A dental adhesive composition as claimed in claim 1, which provides a bonding strength of greater than or equal to 150 kg/cm².

13. A dental adhesive composition as claimed in claim 1 comprising a photopolymerization initiator.

14. A dental adhesive composition as claimed in claim 13, wherein said photopolymerization initiator is camphor quinone.

15. A dental adhesive composition consisting of
   (a) 1-ethyl-3-(3-dimethylaminopropyl)carbodiimide
   (b) at least one methacrylate or acrylate selected from the group consisting of methyl methacrylate, ethyl methacrylate, isopropyl methacrylate, 2-hydroxyethyl methacrylate, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, 2,2-bis(methacryloxyphenyl)propane, 2,2-bis[4-(2-hydroxy-3-methacryloxypropoxy)phenyl]propane, 2,2-bis(4-methacryloxydiethoxyphenyl)propane, 2,2-bis(4-methacryloxypropoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol methacrylate, 1,4-butanediol dimethacrylate, 1,6-hexanediol methacrylate, trimethylolpropane trimethacrylate, trimethylolethane trimethacrylate, pentaerythritol trimethacrylate, trimethylolmethane trimethacrylate, pentaerythritol tetramethacrylate, methacrylates and acrylates containing a urethane bond in their molecules, di-2-methacryloxyethyl-2,2,4-trimethylhexamethylene dicarbamate or its acrylate and compounds having the following structural formula:

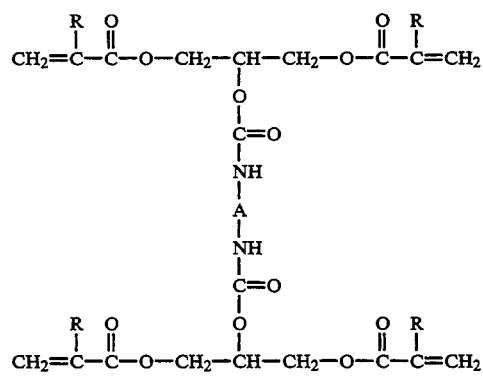

wherein:
R, which may be identical or different from each other is H or CH₃, and
A is —(CH₂)₆—,

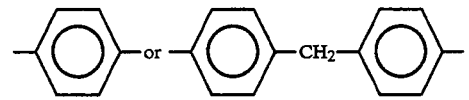

and
(c) a photopolymerization or a chemical polymerization initiator which chemical polymerization initiator is selected from the group consisting of the following combinations:
   1) N-phenylglycine and benzoyl peroxide;
   2) p-toluenesulfinate and benzoyl peroxide; and
   3) p-toluenesulfinate, an aromatic tertiary amine and benzoyl peroxide.

16. A dental adhesive composition as claimed in claim 15, comprising a chemical polymerization initiator.

17. A dental adhesive composition as claimed in claim 16, wherein said chemical polymerization initiator is a combination of N-phenylglycine and benzoyl peroxide.

18. A dental adhesive composition as claimed in claim 15, which provides a bonding strength of greater than or equal to 150 kg/cm².

19. A dental adhesive composition as claimed in claim 15 comprising a photopolymerization initiator.

20. A dental adhesive composition as claimed in claim 19, wherein said photopolymerization initiator is camphor quinone.

* * * * *